United States Patent
Davis

[11] Patent Number: 5,931,670
[45] Date of Patent: Aug. 3, 1999

[54] ILLUMINATED DENTAL SUCTION APPLIANCE

[76] Inventor: James M. Davis, 4687 Pond Apple Dr. South, Naples, Fla. 33999

[21] Appl. No.: 08/959,681

[22] Filed: Oct. 29, 1997

Related U.S. Application Data

[60] Provisional application No. 60/029,664, Oct. 29, 1996.
[51] Int. Cl.[6] ................................................ A61C 17/06
[52] U.S. Cl. ................................................ 433/91; 433/29
[58] Field of Search ................................ 433/29, 31, 91, 433/93, 94, 95, 96; 604/21, 902; 600/156

[56] References Cited

U.S. PATENT DOCUMENTS

| | | | |
|---|---|---|---|
| 3,086,289 | 4/1963 | Orsing | 433/96 |
| 3,541,583 | 11/1970 | Deuschle | 433/96 |
| 4,037,588 | 7/1977 | Heckele | 600/191 |
| 4,204,328 | 5/1980 | Kutner | 433/29 |
| 4,872,837 | 10/1989 | Issalene et al. | 433/29 |
| 4,992,047 | 2/1991 | Warner | 433/91 |
| 5,281,134 | 1/1994 | Schultz | 433/31 |

FOREIGN PATENT DOCUMENTS

3939859  6/1991  Germany ................................ 433/91

*Primary Examiner*—John J. Wilson
*Attorney, Agent, or Firm*—William E. Noonan

[57] ABSTRACT

An illuminated dental suction appliance is disclosed. The appliance includes a suction component having a tubular member and a light projecting tip. The light projecting tip is formed at one end of the tubular member and also at least partially defines an inlet for the tubular member. The opposite end of the tubular member is operably interengaged with a source of suction. Light is transmitted from a fiberoptic illuminator along the length of the tubular member to the light projecting tip. That tip projects light from the illuminator into the patient's mouth.

18 Claims, 3 Drawing Sheets

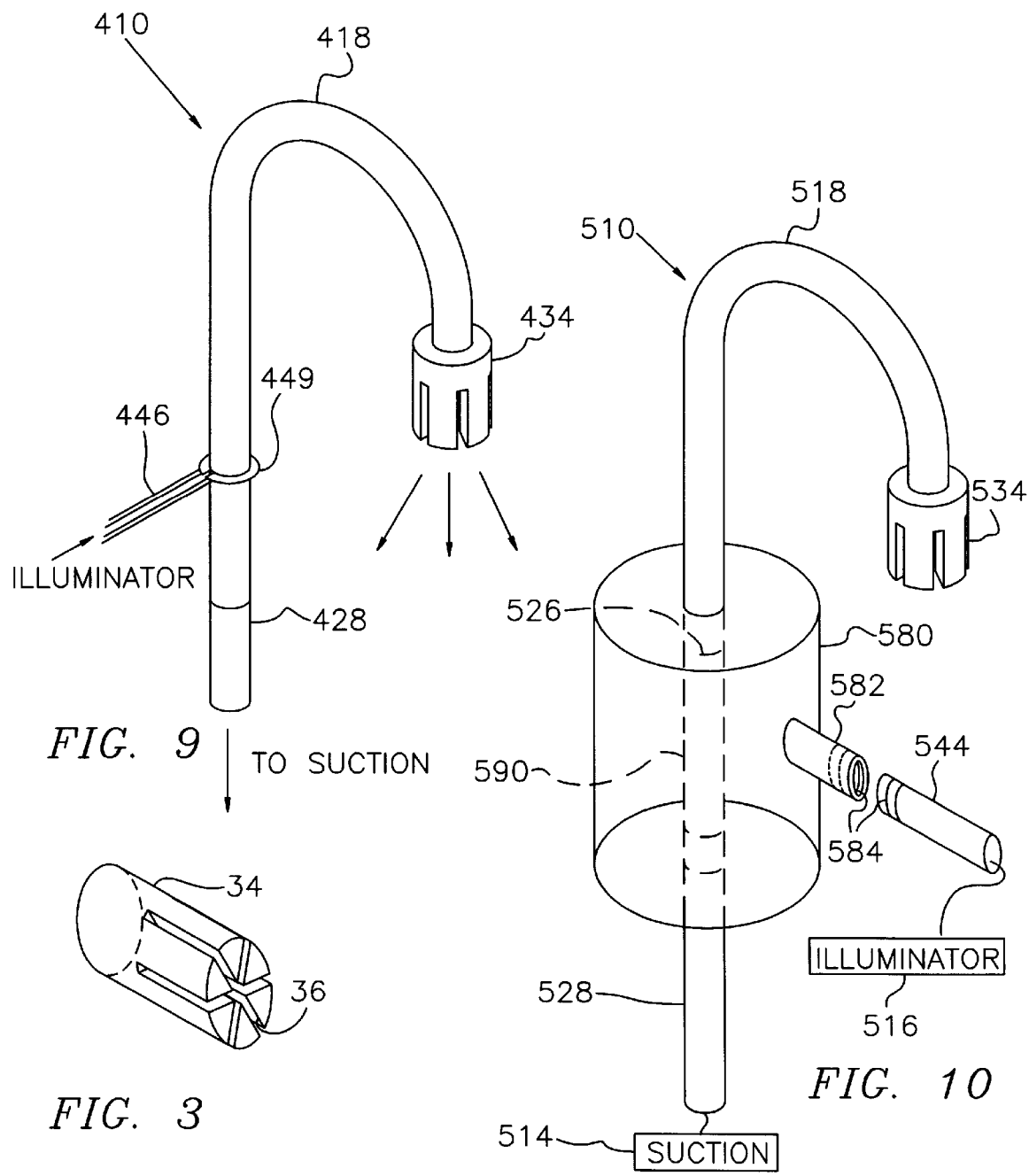

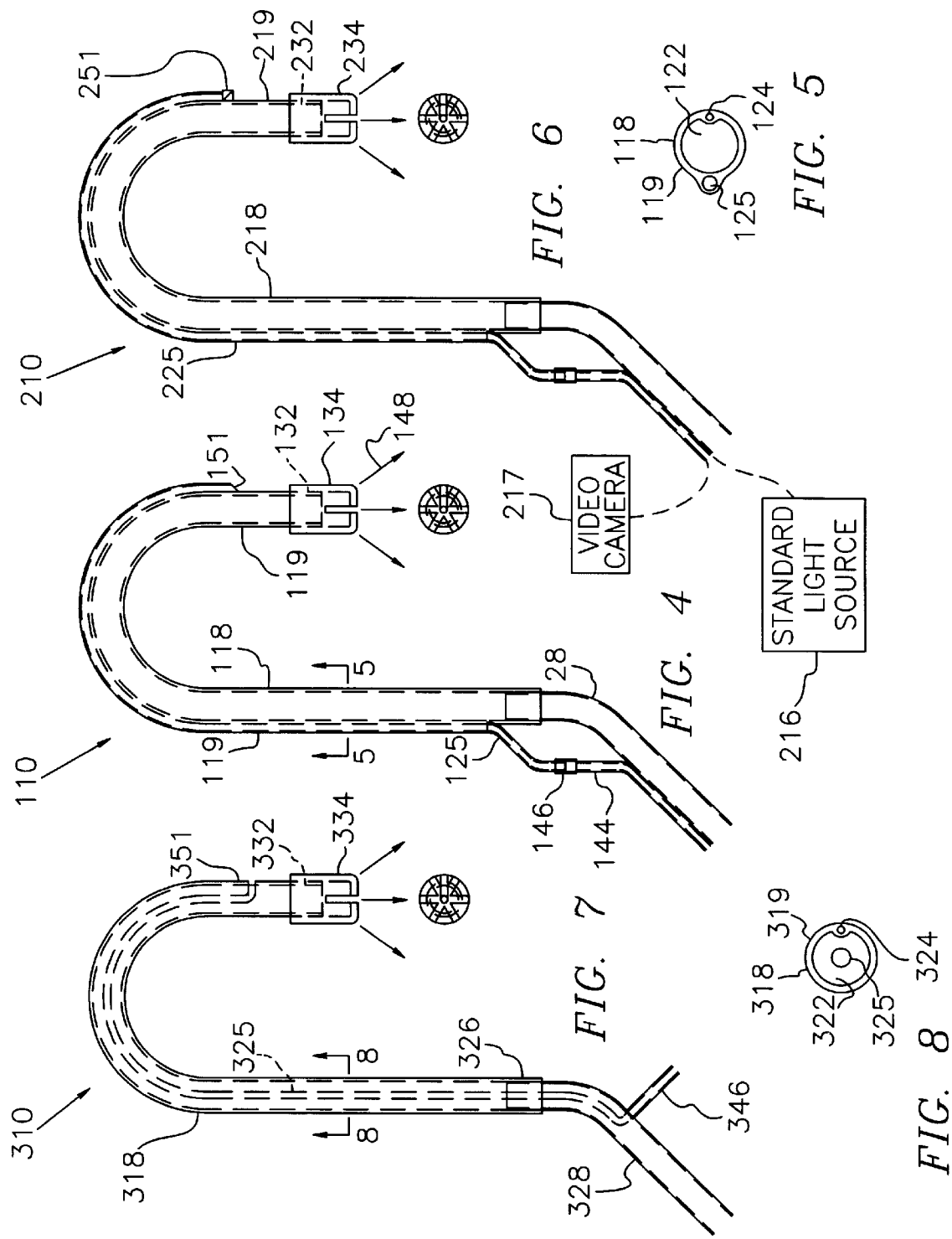

ILLUMINATED DENTAL SUCTION APPLIANCE

RELATED INVENTION

This application claims the benefit of U.S. provisional patent application Ser. No. 60/029,664 filed Oct. 29, 1996.

FIELD OF THE INVENTION

This invention relates to an illuminated dental suction appliance and, more particularly, to a disposable dental suction appliance that is engageable with a fiberoptic light source to illuminate the interior of a dental patient's mouth.

BACKGROUND OF THE INVENTION

Dentists often have a difficult time adequately illuminating the inside of a patient's mouth. Most dentists use an overhead lamp mounted on a pedestal and extending above the patient's chair. Usually, either the dentist or an assistant must frequently adjust the lamp to illuminate the region of the mouth where dental work is being performed. Such adjustments are required because the patient's head may move or the dentist may have to work on a different tooth or in a different location in the mouth. Each time the position of the light needs to be changed, the dental procedure is interrupted. The dentist must then reposition the lamp himself or provide appropriate instructions to his assistant. In either event, manual manipulation of the dental lamp is time consuming and annoying. Moreover, standard overhead dental lamps are located a distance from the mouth and typically do not provide optimal illumination. At present, such lights are only able to illuminate a 28 mm surface within the mouth. This limited area of lighting usually necessitates even further adjustments of the light.

Presently, fiberoptic illuminators are widely employed in medical and surgical procedures. However, dentists only occasionally utilize such illuminators. These instruments typically feature a head lamp that is worn by the physician and tethered by a fiberoptic cable to a light source. Dentists performing work inside the patient's mouth normally dislike wearing an item that ties or tethers them to another instrument. Such an arrangement restricts their freedom of movement during the dental procedure. Furthermore utilizing standard fiberoptic illumination systems requires the purchase and introduction of expensive and sometimes bulky equipment into the dental office.

Fiberoptic lighting has also been attached to dental mirrors used directly inside the patient's mouth. Unfortunately, such illuminated dental mirrors are rather bulky and seriously limit the dentist's working area within the mouth. Additionally, these appliances cannot be rested in the patient's mouth, and instead, must be constantly held and manipulated by the dentist. Fiberoptically lighted mirrors too are tethered to a light source and tend to restrict dentist's movement.

SUMMARY OF INVENTION

It is therefore an object of this invention to provide an illuminated dental suction device that quickly, simply and effectively illuminates the interior of a dental patient's mouth without requiring the use of standard fiberoptic illumination equipment.

It is a further object of this invention to provide an illuminated dental appliance that projects light into a dental patient's mouth with much greater intensity and effectiveness than is accomplished using standard dental lamps.

It is a further object of this invention to provide an illuminated dental suction appliance that eliminates the interruption, inconvenience and annoyance that normally accompany having to frequently adjust an overhead dental lamp to properly illuminate selected areas of a patient's mouth.

It is a further object of this invention to provide an illuminated dental suction appliance that is relatively inexpensive, readily disposable, and easy to assemble, disassemble and replace, such that each successive patient is provided with a fresh appliance.

It is a further object of this invention to provide an efficient dental appliance that consolidates suction and lighting functions.

It is a further object of this invention to provide an illuminated dental suction appliance which minimizes the amount of dental equipment placed in a patient's mouth so that the dentist is given increased room to work within the oral cavity.

It is a further object of this invention to provide a dental appliance which utilizes the suction device to illuminate the inside of the patient's mouth thereby more efficiently utilizing the space occupied by the suction device.

This invention results from a realization that significantly improved proximate lighting of the inside of a dental patient's mouth is achieved and, at the same time, annoying lamp adjustments are eliminated by utilizing a dental suction appliance as an illuminator. This invention results from the further realization that such illumination is most effectively achieved by using a fiberoptic conductor to operably interconnect the suction appliance with a light source. Light from the light source is transmitted through the fiberoptic conductor and the suction device and projected from that device to illuminate the patient's mouth.

The invention features an illuminated dental suction appliance that includes a suction assembly. The suction assembly comprises an elongate tubular member having a first end that is operably interengaged with a source of suction. Means carried at an opposite second end of the tubular member define an inlet that is placed within a dental patient's mouth. The source of suction causes fluids within the mouth, typically saliva, blood and rinse water, to be pulled into the tube through the inlet and toward the suction for disposal of such material. A light projecting component is carried by the tubular member proximate the inlet. A source of light is interconnected by a light conductor to the suction assembly. There are light transmitting means carried by the elongate tube for optically interconnecting the light conductor and the light projector component. This transmits the light from the light source to the light projecting component. Such light is projected into the patient's mouth to illuminate that region.

In a preferred embodiment, the elongate tubular member includes a hooked portion that engages the patient's lip. The light projecting component may comprise a portion of the elongate tubular member proximate the inlet. The projector component may also comprise a generally bulbous or otherwise enlarged tip element through which the inlet is formed. Preferably, this tip element is transparent and includes an effective light projecting material. The tip may be formed either unitarily with, or separately from, the elongate tubular member.

The means for transmitting light from the light conductor to the light projector may take one of various different forms. Such means for transmitting may include the wall of elongate tubular member. That member may include a transparent, light conducting material. In such cases, the tubular member may either be fully transparent or coated with an opaque substance. Fully transparent tubular members should be composed of a material that exhibits minimal radial diffusion or dispersion of light. The suction component may include a branch fitting that is attached to the elongate light conducting member. The branch fitting effectively forms a "Y" junction with the first end of the elongate member.

Alternatively, the means for transmitting may include a light transmitting optical fiber that is attached to and extends along the elongate tubular member. The optical fiber may extend through a longitudinal channel formed in the tubular member. The distal end of the optical fiber is communicably attached to the tubular member proximate the light projecting portion such that light is transmitted from the means for transmitting and to the light projector. The means for conducting may include a light conducting tube that is secured to the optic fiber by various means of attachment such as a "lure lock".

The means for transmitting may alternatively include an optical fiber that extends longitudinally through a central opening of the tubular member. A first end of the optical fiber is interconnected to a light source by a light conducting tube. This tube is formed through the side wall of a suction tube that is communicably joined to the elongate tube of the suction appliance. A distal end of the optical fiber is optically interconnected to the elongate tube proximate the suction inlet. This optical fiber delivers light centrally through the elongate tubular member to a projecting member carried at the distal end of the elongate tubular member.

Typically, the elongate tubular member carries an elongate, flexible shaping element that maintains a selected shape into which the flexible element is flexed. This permits the tubular element to be bent and formed into a hook shape so that it properly and comfortably engages the patient's mouth.

DETAILED DESCRIPTION OF PREFERRED EMBODIMENTS

Other objects, features and advantages will occur from the following description of preferred embodiments and the accompanying drawings, in which:

FIG. 3 is a perspective view of a preferred light projecting tip component employed by the suction appliance;

FIG. 4 is an elevational side view of an alternative preferred suction appliance according to this invention;

FIG. 5 is a cross sectional view taken along line 5—5 of FIG. 4;

FIG. 6 is an elevational side view of a third version of the suction appliance;

FIG. 7 is an elevational side view of a fourth version of the suction appliance;

FIG. 8 is a cross sectional view taken along line 8—8 of FIG. 7;

FIG. 9 is a perspective view of a fifth version of the suction appliance; and

FIG. 10 is a perspective, partly schematic view of a sixth version of the suction appliance, which version utilizes a transparent handle.

Figures 1, 2:
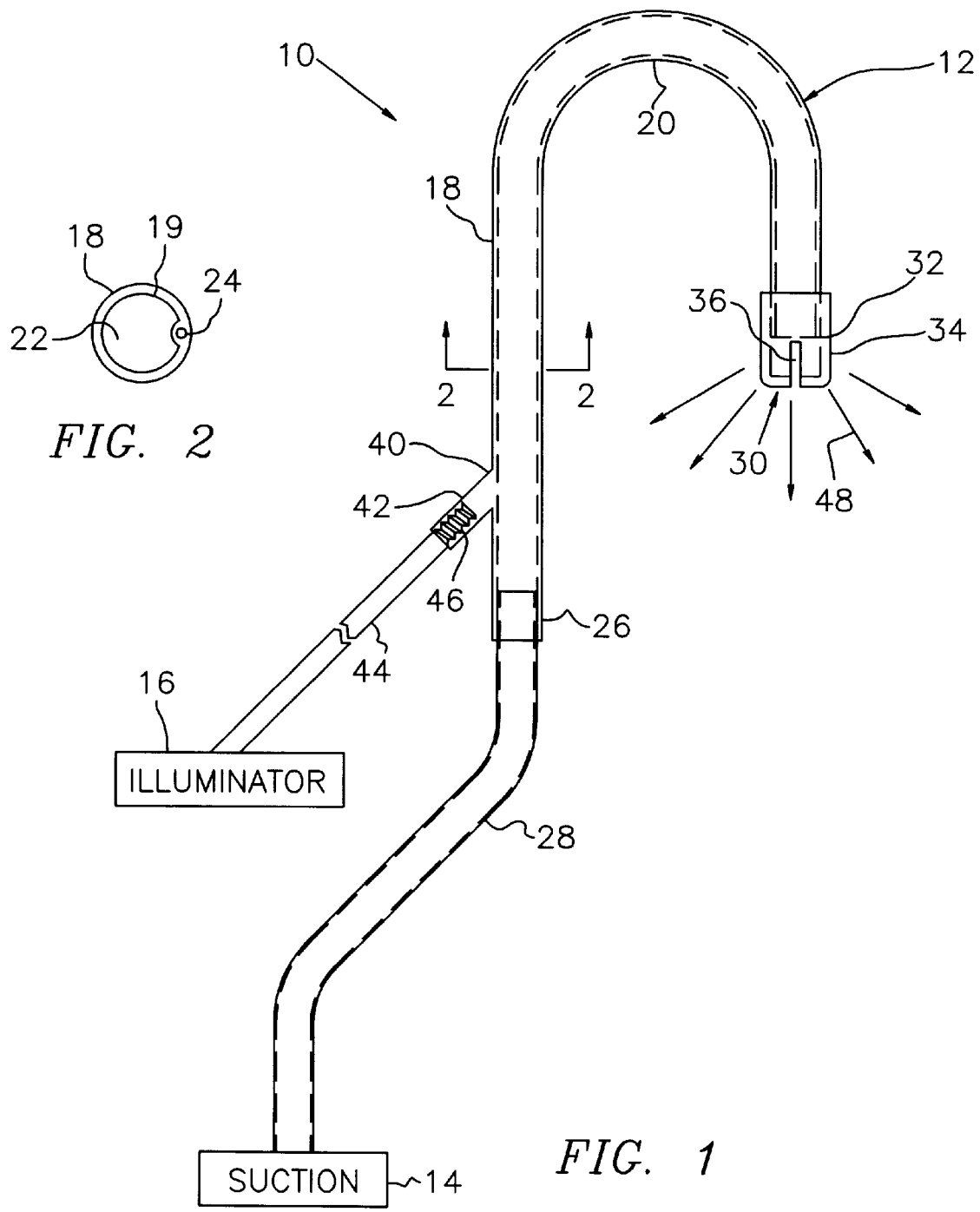
FIG. 1 is an elevational, partly schematic view of a preferred illuminated dental suction appliance according to this invention.
FIG. 2 is a cross sectional view taken along line 2—2 of FIG. 1.

There is shown in FIG. 1 a dental suction appliance 10 that is used to illuminate the interior of a dental patient's mouth so that appropriate dental work may be performed. Appliance 10 includes a disposable suction component 12 that is releasably interconnected to both a conventional suction source 14 and an illuminator device 16. Suction source 14 comprises a standard dental suction apparatus that will be known and understood to persons skilled in the art. Illuminator 16 comprises a standard fiberoptic illuminator having a halogen, neon or other known type of light source. Suction component 12 includes an elongate tubular member 18 composed of a preferably transparent or other light conducting plastic material. Tubular member 18 is lightweight and flexible. The tubular member is curved to include a hook portion 20. As shown in FIG. 2, member 18 has a tubular wall 19 and a central bore 22. Wall 19 carries an elongate, bendable shaping element 24 comprising wire or similar material. Element 24 should be flexible and able to maintain the condition into which it is flexed. This permits tubular member 18 to be formed into the curved or hooked shape shown in each of the embodiments herein. See, in particular, hooked portion 20 in FIG. 1. The material comprising the elongate element should be appropriate for use in a dental patient's mouth.

A first, lower end 26 of tubular member 18 has an opening that receives one end of a suction conduit 28. The other end of suction conduit 28 is communicably and operably interconnected to suction source 14. Proximate the opposite, upper end of tubular member 18, the suction component 12 includes an inlet 30. More particularly, end 32 of tubular member 18 carries an enlarged or bulbous tip 34, which is shown alone in FIG. 3. Tip 34 comprises a transparent and light projecting material. This material should likewise be suitable for insertion into a dental patient's mouth. The light projecting tip may be removable from tubular member 18. Alternatively, it may be formed unitarily with tube 18 and comprise a distal portion of the tube surrounding inlet 30. In either case, the inlet is formed into the tube through tip 34. The tip includes a plurality of slots 36 that are formed radially in the distal end of tip 34 and extend longitudinally for at least a portion of the length of the tip. As best shown in FIG. 1, tip 34 includes an interior cavity that receives the open upper end 32 of tubular member 34. As a result, the slotted tip 34 and the open upper end 32 of tubular member 18 define an inlet 30 through which saliva, blood and water are sucked into appliance 10. Hook 20 is engaged with a patient's lip and tip 34 is introduced into the patient's mouth. Suction 14 is operated so that liquids are drawn from the mouth through slots 36 into tubular member 18 and, from there, into a conventional disposal system or container. This portion of the apparatus and its function are known and essentially exhibited by previous dental suction appliances.

The performance of the dental suction appliance is improved considerably by the incorporation of illumination into the appliance. In particular, illuminator 16 is operably interconnected to suction component 12 in the following manner. The suction component 12 includes a "Y" junction 40 proximate the lower end of tubular member 18. The "Y" junction includes a branch element 42 that is unitarily interconnected to and branches off from tubular member 18. Branch 42 comprises the same material which forms the tubular member and is typically unitarily formed with the tubular member in a molding process. The branch element includes a transparent or other light conducting material. A light conducting tube or fiber 44 is releasably engaged with branch 42 by means of complementary threads 46 or some other type of coupling structure. The opposite end of fiber 44 is optically engaged with illuminator 16. As a result, fiber 44 conducts light from illuminator 16 to branch 42 and thereby to suction component 12. The end of fiber 44 that is attached to branch 42 comprises a light outlet, which projects light in a narrow beam into branch 42. The branch conducts this light to the light transmitting wall 19 of tubular member 18. As a result, light is transmitted along the length of member 18 to upper end 32 and light projecting tip 34, which are located in the patient's mouth. Light is projected, in the manner indicated by arrows 48 from tip 34 so that the interior of the patient's mouth is brightly illuminated. The dentist can then readily perform necessary dental work. The light is projected from an appliance directly within the patient's mouth. Constant adjustment of a remote dental lamp and the annoying interruptions that typically accompany this procedure are therefore avoided.

To effectively transmit the light from fiber 44 to tip 34, suction component 12 should be composed of a material that effectively conducts the light along the length of tube 18, but does this with a minimum of radial light loss. To accomplish this, a transparent material may be employed. A coating may be applied on the outer surface of the transparent material to minimize diffusion and dispersion of the light. Alternatively, a transparent, light conducting material that inherently exhibits minimal radial light dispersion may be used.

A particularly beneficial feature of this invention is the disposability of suction component 12. The flexed tubular member and unitary branch element are mass produced through a molding process which minimizes the manufacturing time and expense. Likewise, the tip is preferably molded. In alternative embodiments, the tip may be formed unitarily with the tubular member. Various sizes and shapes of tips may be utilized. A generally cylindrical shape is shown in FIG. 1. However, in alternative embodiments, a more bulbous shape may be utilized. After each use, suction component 12 may be readily detached, disposed of and replaced with a new suction component. Replacement is performed simply by detaching fiber 44 from branch 42 and removing end 26 of tubular member 18 from suction conduit 28. A new suction component 12 is then installed by re-engaging fiber 44 and suction conduit 28 with the branch 42 and tubular member 18, respectively, of the new suction component. Although disposability is preferred, in certain embodiments, a more permanent suction component, which is sterilized between patients, may be utilized. In still other embodiments, simply the light projecting tip 34 may be replaced.

Various alternative embodiments of the illuminated dental suction appliance are illustrated in FIGS. 4–10. It should be understood that each of the alternative versions uses a standard illuminator and suction source, as previously described. Device 110, FIG. 4, employs an elongate tubular member 118 that receives and is communicably engaged with the upper end of a suction conduit 28. As best shown in FIG. 5, member 118 includes a tubular wall 119 and a central bore 122. A bendable shaping wire 124 again extends through wall 119 so that the user can flex the tubular member 118 into the desired hook shape shown in FIG. 4. In this version, a light conducting fiber 125 is run through tubular wall 119 on the opposite side of the bore from bending element 124. As best shown in FIG. 4, a lower end of fiber 125 exits tubular wall 119 and is releasably interconnected to a light conducting fiber 144 through an appropriate connector 146. Again, this connector may comprise complementary threads, a receptacle, "lure lock" or other known means for communicably and operably interconnecting optical fibers. Light conductor 44 extends along suction conductor 28 and is optically joined with a standard fiberoptic illuminator, not shown.

In the version of FIGS. 4 and 5, light is directed through fiber 144 and into fiber 125. The light is transmitted through the latter fiber along the length of tubular member 118. At end 151, the light is transmitted into the tubular wall 119. As in the previously described embodiment, this wall comprises a light transmitting material. As a result, the light from fiber 125 is transmitted through end 132 of tubular wall 119 into a light projecting tip 134. This tip is identical or at least similar to the tip of the previously described version. Tip 134 projects the light in the manner indicated by arrows 148 into the patient's mouth.

In this alternative version, replaceability and disposability are again important advantages. Appliance 110 is detached simply by pulling tube 118 off of suction conduit 28 and detaching fiber 125 from fiber 144. A sterile replacement suction component is then installed by reattaching new member 118 and fiber 125 with suction conduit 28 and optical fiber 144, respectively.

FIG. 6 discloses another alternative version of the dental suction appliance 210. This embodiment is very similar to the embodiment shown in FIGS. 4 and 5. The only distinction is that a small lens 251 is formed at the upper end of the optical fiber 225 that extends along tubular member 218. Lens 251 directs the light that is transmitted from source 216 through fiber 225 into the light transmitting wall 219 of member 218. This light is transmitted through end portion 232 into light projecting tip 234. The tip projects this light into the patient's mouth in the manner previously described. Alternatively, fiber 225 may transmit light from a lighted video camera or other type of lighted fiber scope 217 to lens 251. Images from inside the mouth may then be transmitted through fiber 225 to camera 217. Accordingly, the suction device may be used as part of an optical scope for monitoring the inside of a patient's mouth. Various types of lens structures may be mounted to the suction device proximate the inlet.

FIG. 7 illustrates a dental appliance 310 having a tubular member 318 that closely resembles the tubular member utilized in the embodiment of FIG. 1. As shown in FIG. 8, tubular member 318 features a generally cylindrical wall 319 and a central bore 322. A bending wire 324 is again extended through wall 319. The bending wire permits tubular member 318 to be bent into the hook shape shown in FIG. 7 so that the dental appliance may be engaged with and held in place in the patient's mouth.

A light transmitting optical fiber 325 extends longitudinally through bore 322 of tubular member 318. More particularly, as shown in FIG. 7, a light conducting fiber 346 is attached to the side wall of suction conduit 328. The suction conduit is operably attached at one end to a suction source in the manner previously described. The opposite end of suction conduit 328 is engaged with the lower end 326 of tubular member 318. Light conduit 346 is operably engaged at its opposite end with a fiberoptic illuminator, not shown. Fiber 346 is interconnected through the side wall of suction conduit 328 with light transmitting fiber 325. The light transmitting fiber extends through bore 322 for most of the length of tubular member 318 and is operably attached to member 318 at a point 351 of tubular wall 319 proximate the upper end of the tubular member. A light projecting tip 334 is again attached to the upper end 332 of tubular member 318. The tubular member includes a light transmitting material. As a result, light transmitted through fiber 325 is delivered to the tubular member at point 351. The wall 319 of tubular member 318 transmits this light to end 332 and into light projecting tip 334. The tip again projects light into the patient's mouth.

Illuminated suction appliance 410, shown in FIG. 9, similarly includes a hooked tubular member 418, which is constructed in the manner previously described for the tubular members in FIGS. 1 and 7. In this version, the wall of the tubular member comprises a light conducting material similar to the version in FIG. 1. Light is delivered from an illuminator through an optical fiber 446 to a light transmitting ring 449 that is wrapped about tubular member 418. Light is emitted from ring 449 into the wall of tubular member 419. The tubular member then transmits this light in the manner described in FIG. 1 to the light projecting tip 434, which in turn projects light into the dental patient's oral cavity. The version of FIG. 9 operates in basically the same manner as the versions described above. Tubular member 418 and tip 434 are fully disposable. The tubular member is releasably engaged to a suction line 428 that is itself connected to a standard source of suction.

In the version of FIG. 10, illuminated dental appliance 510 again includes a hook-shaped tubular member 518 and a light projecting suction tip 534. The lower end of tubular member 518 is detachably interconnected to a handle component 580. The handle component is transparent or otherwise includes a light transmitting material. A light transmitting connector branch 582 extends from the side of handle 580. A light transmitting fiber 544 is operably engaged with a standard illuminator 516 and is selectively and operably interengaged with connector 582 through appropriate connection means such as complementary threads 584.

The lower end 526 of tubular member 518 is received in a central opening 590 of handle 580. The opposite end of central opening 590 receives the upper end of a suction conduit 528, which is itself operably engaged with a suction source 514.

In operation, the tubular member 518 is interengaged with handle 580 and optical fiber 544 is similarly interengaged with connector 582 of handle 580. Light is thereby provided to the handle which transmits this light to tubular member 518. The tubular member again includes light transmitting material that conducts the light to the light projecting tip 534. The suction source 514 is operated in a conventional manner. As a result, when appliance 510 is placed in the patient's mouth and activated, the interior of the mouth is illuminated and blood, saliva and water are removed from the mouth.

A critical aspect of the present invention is that the light is delivered through and projected from the tubular suction assembly itself, unlike devices of the prior art wherein the light is projected from an element separate and distinct from the suction tube. In the present invention, the inlet extends through the light projecting component, which may be either separable from or unitary with the tube. As a result, light is projected in essentially a circular pattern about the inlet. This provides for much improved lighting and visibility within the patient's oral cavity.

It should be understood that, in still other versions, the handle may be formed permanently with the tubular member. In all versions of this invention, a more permanent structure may be built within the spirit of this invention. It is only required that some source of lighting be provided to the suction tube. The appliance must also include some means for effectively projecting the light into the patient's mouth so that the area being worked upon is properly illuminated. Lighted video cameras and other optical scopes may be used in conjunction with the light source and the light transmission means. Various other versions may also be employed within the spirit and scope of this invention.

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. An illuminated dental suction appliance comprising:

a suction assembly including an elongate tubular member, which has a first end that is operably interengaged with a source of suction, said tubular member including a tubular wall composed of a light conducting material;

means, carried at an opposite second end of said tubular member, for defining an inlet that is placed within a dental patient's mouth, said source of suction causing fluids within the mouth to be pulled into said tubular member through said inlet and toward said suction source;

a light projecting component including a tip element composed of a light conducting and projecting material that is carried by said tubular member and through which said inlet is formed;

a fiberoptic light conductor that is operably connected to a fiberoptic light source; and;

a fitting unitarily connected to said wall of said tubular member, said light conductor being communicably and releasably connected to said fitting to deliver light from said light source through said fitting to said wall of said tubular element, whereby light is transmitted longitudinally through said tubular element by the material composing said wall to said tip, which tip projects light into and illuminates the patient's mouth.

2. The appliance of claim 1 in which said tubular member includes a hooked portion that engages the patient's lip.

3. The appliance of claim 1 in which said light projecting component includes a portion of said tubular member proximate said inlet.

4. The appliance of claim 1 in which said light projecting component includes a tip element, which is enlarged relative to said tubular member.

5. The appliance of claim 1 in which said tubular member is at least partly coated to restrict light dispersion through said member.

6. The appliance of claim 1 in which said light projecting component is transparent.

7. The appliance of claim 1 in which said tubular member includes a branch fitting that is attached to said fiberoptic light conductor.

8. The appliance of claim 1 in which said fiberoptic light conductor includes a light transmitting optical fiber that is attached to and extends along said tubular member.

9. The appliance of claim 8 in which said optical fiber extends through a longitudinal channel formed in said tubular member, a distal end of said optical fiber being communicably attached to said tubular member proximate said light projecting component such that light is transmitted from said means for transmitting to said light projecting component.

10. The appliance of claim 8 in which said means for conducting include a light conducting tube that is releasably secured to said optical fiber.

11. The appliance of claim 1 in which said fiberoptic conductor includes an optical fiber that extends longitudinally through a central opening of said tubular member.

12. The appliance of claim 11 in which said optical fiber includes a first end that is interconnected to said light source by a light conducting tube.

13. The appliance of claim 12 in which said light conducting tube is formed through a side wall of a suction tube that is communicably joined to said tubular member of said suction assembly a distal end of said optical fiber being optically interconnected to said tubular member proximate said suction inlet.

14. The appliance of claim 1 in which said elongate tubular member carries an elongate, flexible shaping element that maintains a selected shape into which said flexible element is flexed.

15. The appliance of claim 1 in which said fitting is composed of a light conducting material.

16. An illuminated dental suction appliance comprising:

a suction assembly including an elongate tubular member, which has a first end that is operably interengaged with a source of suction, said tubular member including a tubular wall composed of a light conducting material;

means, carried at an opposite second end of said tubular member, for defining an inlet that is placed within a dental patient's mouth, said source of suction causing fluids within the mouth to be pulled into said tubular member through said inlet and toward said suction source;

a light projecting component including a bulbous, tip element composed of a light conducting and projecting material that is carried by said tubular member and through which said inlet is formed;

a fiberoptic light conductor that is operably connected to a fiberoptic light source and;

a fitting unitarily connected to said wall of said tubular member, said light conductor being communicably and releasably connected to said fitting to deliver light from said light source through said fitting to said wall of said tubular element, whereby light is transmitted longitudinally through said tubular element by the material composing said wall to said tip, which tip projects light into the patient's mouth in a circular pattern about said inlet to illuminate the mouth.

17. The appliance of claim 16 in which said fitting is composed of a light conducting material.

18. An illuminated dental suction appliance comprising:

a suction assembly including an elongate tubular member, which has a first end that is operably interengaged with a source of suction;

means, carried at an opposite second end of said tubular member, for defining an inlet that is placed within a dental patient's mount; said source of suction causing fluids within the mouth to be pulled into said tubular member through said inlet and toward said suction source;

a light projecting component carried by said tubular member and through which said inlet is formed;

a light conductor, which interconnects a source of light to said suction assembly; and means, carried by said tubular member, for optically interconnecting said light conductor and said light projecting component and transmitting light from said light source to said light projecting component, which component projects light into and illuminates the patient's mouth; said means for transmitting including an optical fiber that extends longitudinally through a central opening of said tubular member, said optical fiber including a first end that is interconnected to said light source by a light tube, said light tube being formed through a side wall of a suction tube that is communicably joined to said tubular member of said suction appliance, a distal end of said optical fiber being optically interconnected to said tubular member proximate said suction inlet.

\* \* \* \* \*